US00PP09020P

United States Patent [19]

VandenBerg

[11] Patent Number: Plant 9,020

[45] Date of Patent: Dec. 20, 1994

[54] CHRYSANTHEMUM PLANT NAMED JULIA

[75] Inventor: Cornelis P. VandenBerg, Salinas, Calif.

[73] Assignee: Yoder Brothers, Inc., Barberton, Ohio

[21] Appl. No.: 169,188

[22] Filed: Dec. 20, 1993

[51] Int. Cl.[5] ..... A01H 5/00

[52] U.S. Cl. ..... Plt./82.2

[58] Field of Search ..... Plt. 82.2, 78

*Primary Examiner*—Howard J. Locker

*Attorney, Agent, or Firm*—Foley & Lardner

[57] ABSTRACT

A Chrysanthemum plant named Julia particularly characterized by its flat capitulum form; daisy capitulum type, with 4 to 5 rows of ray florets; yellow ray floret color; diameter across face of capitulum of 50 to 60 mm when fully opened; branching pattern is spreading and prolific, with 9 breaks after pinch when grown outside under natural daylength in fall flowerings and 5 to 7 breaks when grown in 10 cm pots for spring flowerings; natural season flower date of August 23 to September 3 when planting rooted cuttings on June 21 to 25 in Salinas, Calif., and October 3 to 10 when planting rooted cuttings June 11 to June 18 in Hightstown, N.J.; flowering response of 46 to 49 days after rooting in no light/no shade programs in spring in Salinas; plant height of 23 to 30 cm when grown in fall under natural daylength with no growth regulators in New Jersey, and 13 to 18 cm when grown in 10 cm pots in spring with no growth regulator applications; and recommended for spring and late season fall variety.

3 Drawing Sheets

The present invention comprises a new and distinct cultivar of Chrysanthemum, botanically known as *Dendranthema grandiflora,* and referred to by the cultivar name Julia.

Julia, identified as 8783 (90-67005) was originated from an open pollination program, where the best breeding lines were selected by Cornelis P. VandenBerg, flowered under controlled conditions outdoors and left to be pollinated by bees, in Salinas, Calif. in September 1989.

The female parent of Julia was an unnamed seedling identified as 9430 (88336001), and described as a garden mum having yellow ray floret color and daisy capitulum type. The female parent was discarded from all programs in November 1990.

The male parent of Julia is unknown, since the female parent of Julia was open pollinated.

Julia was discovered and selected as one flowering plant within the progeny of the stated cross by Cornelis P. VandenBerg in November 1990, in a controlled environment in Salinas, Calif.

The first act of asexual reproduction of Julia was accomplished when vegetative cuttings were taken from the initial selection in January 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Julia are firmly fixed and are retained through successive generations of asexual reproduction.

Julia has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Julia, which, in combination, distinguish this Chrysanthemum as a new and distinct cultivar:

1. Flat capitulum form.
2. Daisy capitulum type, with 4 to 5 rows of ray florets.
3. Yellow ray floret color.
4. Diameter across face of capitulum of 50 to 60 mm when fully opened.
5. Branching pattern is spreading and prolific, with 9 breaks after pinch when grown outside under natural daylength in fall flowerings and 5 to 7 breaks when grown in 10 cm pots for spring flowerings.
6. Natural season flower date of August 23 to September 3 when planting rooted cuttings on June 21 to 25 in Salinas, Calif., and October 3 to 10 when planting rooted cuttings June 11 to June 18 in Hightstown, N.J.
7. Flowering response of 46 to 49 days after rooting in no light/no shade programs in spring in Salinas.
8. Plant height of 23 to 30 cm when grown in fall under natural daylength with no growth regulators in New Jersey, and 13 to 18 cm when grown in 10 cm pots in spring with no growth regulator applications.
9. Recommended for spring and late season fall variety.

The accompanying photographic drawings show typical inflorescence and leaf characteristics of Julia, with the colors being as nearly true as possible with illustrations of this type.

Sheet 1 is a color photograph of Julia grown as a pinched garden mum under natural season outside in Salinas, Calif. Plants were grown outside and dug and transplanted into 15 cm bulb pans at flowering time for photography purposes.

Sheet 2 is a black and white photograph of three views of the inflorescence of Julia.

Sheet 3 is a black and white photograph showing the upper and under sides of the leaves of Julia at 3 stages of development (mature, intermediate and immature). In sheets 2 and 3 a measuring tape in centimeters has been added.

Of the commercial cultivars known to the inventor, the most similar in comparison to Julia is the cultivar identified as Anna, disclosed in U.S. Plant Pat. No. 7,847. Reference is made to attached Chart A, which compares certain characteristics of Julia to the same characteristics of Anna.

Similar traits are ray floret color, capitulum form and branching pattern. Julia has a daisy capitulum type, while Anna has a spooned daisy capitulum type, with Julia having a higher number of ray florets than Anna. When compared with Anna, Julia has a smaller diameter of capitulum, a later natural season flower date in the fall, an earlier controlled response in spring flowerings and shorter plant height in both spring and fall flowering than Anna.

In the following description, color references are made to The Royal Horticultural Society Colour Chart. The color values were determined on plant material grown as a pinched garden mum grown outdoors in Salinas, Calif. on Aug. 24, 1993.

Classification:

*Botanical.*—*Dendranthema grandiflora* cv Julia.

*Commercial.*—Flat daisy spray pot mum and garden mum.

INFLORESCENCE

A. Capitulum:

*Form.*—Flat.

*Type.*—Daisy.

*Diameter across face.*—50 to 60 mm when fully opened.

B. Corolla of ray florets:

*Color (general tonality from a distance of three meters).*—Yellow.

*Color (upper surface).*—9A.

*Color (under surface).*—7B.

*Shape.*—See photograph.

C. Corolla of disc florets:

*Color (mature).*—14B.

*Color (immature).*—151A.

D. Reproductive organs:

*Androecium.*—Present on disc florets only; moderate pollen.

*Gynoecium.*—Present on both ray and disc florets.

PLANT

A. General appearance:

*Height.*—Plant height of 23 to 30 cm when grown in fall under natural daylength in New Jersey with no growth regulators, and 13 to 18 cm when grown in 10 cm pots in spring with no growth regulator applications.

*Branching pattern.*—Spreading, with 9 breaks after pinch when grown outside under natural daylength in fall flowerings and 5 to 7 breaks when grown in 10 cm pots for spring flowerings.

B. Foliage:

*Color (upper surface).*—147A.

*Color (under surface).*—147B.

*Shape.*—See photograph.

CHART A

| | JULIA | ANNA |
|---|---|---|
| Ray floret color | Yellow | Yellow |
| Capitulum form and type | Flat daisy | Flat spooned daisy |
| Diameter across face of capitulum | 50 to 60 mm | 57 to 76 mm |
| Branching pattern | Spreading and prolific | Spreading and prolific |
| Natural season flower date: | | |
| in Salinas, CA | Aug 23 to Sep 3 | Aug 16 to 25 |
| in Hightstown, NJ | Oct 3 to 10 | Sep 17 to Oct 1 |
| Controlled response | 46 to 49 days | 49 to 53 days |
| Plant height: | | |
| in natural season fall | 23 to 30 cm | 30 to 36 cm |
| in 10 cm pots spring | 13 to 18 cm | 18 to 20 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Julia, as described and illustrated.

* * * * *

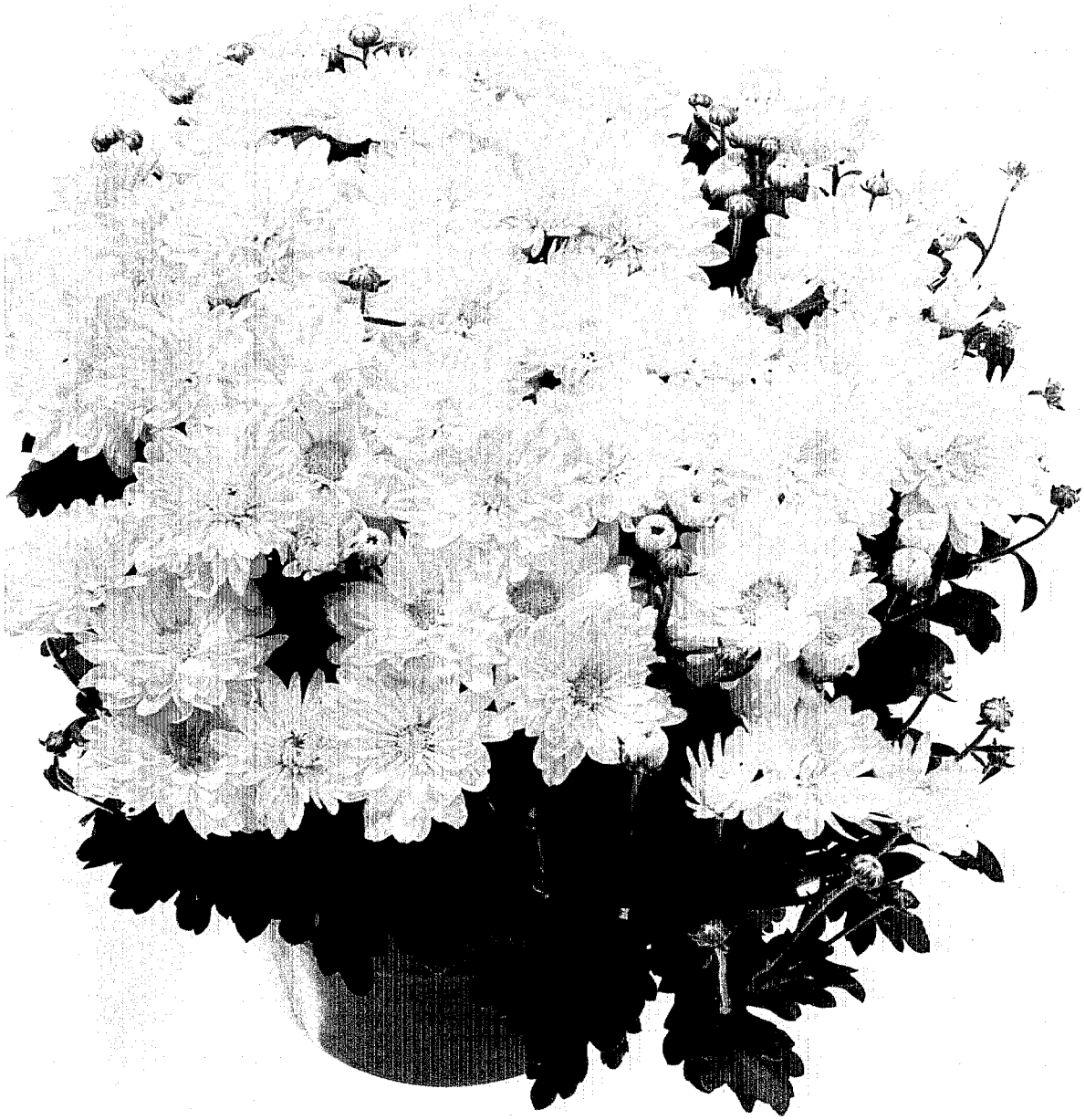

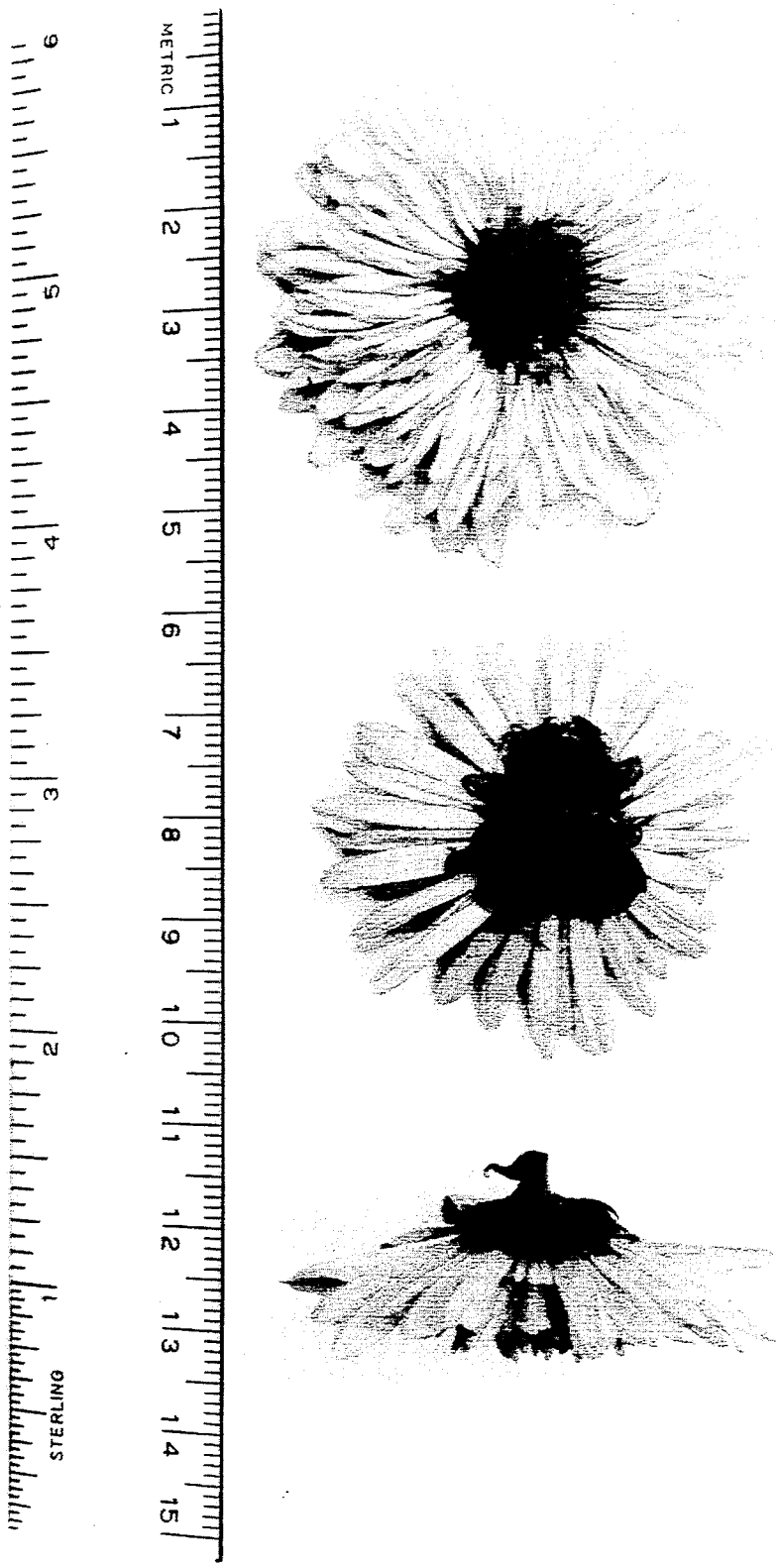
METRIC
STERLING

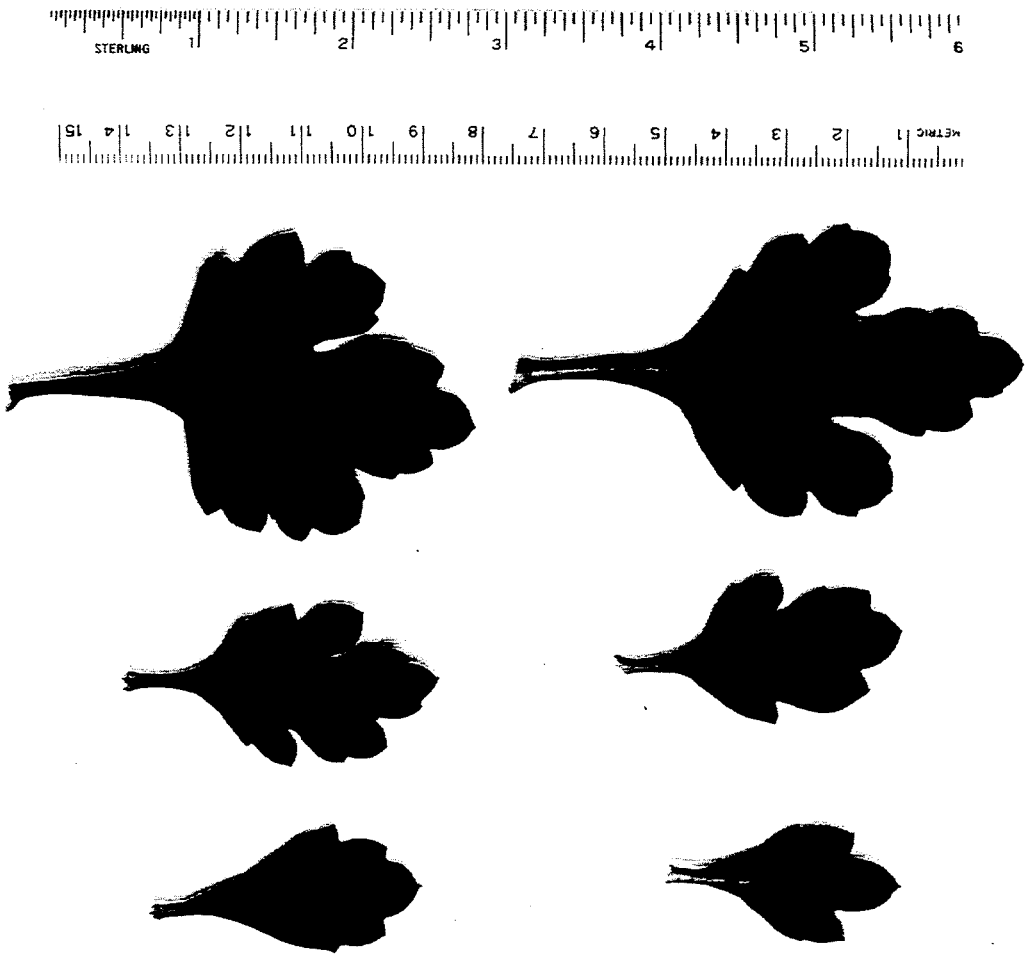
STERLING
1
2
3
4
5
6
METRIC
1
2
3
4
5
6
7
8
9
10
11
12
13
14
15